United States Patent [19]

Wehrmeister

[11] 4,200,646
[45] Apr. 29, 1980

[54] METHOD OF CONTROLLING THE GROWTH OF MICROORGANISMS USING NITROALKYL THIOCYANATES

[75] Inventor: Herbert L. Wehrmeister, Terre Haute, Ind.

[73] Assignee: International Minerals & Chemical Corporation, Terre Haute, Ind.

[21] Appl. No.: 10,187

[22] Filed: Feb. 7, 1979

[51] Int. Cl.$^2$ ...................... A01N 9/18; C07C 161/02
[52] U.S. Cl. ..................................... 424/302; 260/454
[58] Field of Search .......................... 260/454; 424/302

[56] References Cited

PUBLICATIONS

Noller, Textbook of Organic Chemistry, W. B. Saunders Company, 1958, p. 199.

Reid, Organic Chemistry of Bivalent Sulfur, vol. VI, Chemical Publishing Company, Inc., 1966, p. 40.

Primary Examiner—Henry R. Jiles
Assistant Examiner—Robert C. Whittenbaugh
Attorney, Agent, or Firm—Robert H. Dewey; Howard E. Post

[57] ABSTRACT

A method of controlling the growth of microorganisms by using a compound represented by the formula

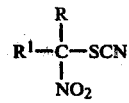

wherein R is hydrogen or methyl, $R^1$ is hydrogen, methyl or ethyl, or R and $R^1$ can collectively be a cyclic alkyl group of 5 carbon atoms.

7 Claims, No Drawings

METHOD OF CONTROLLING THE GROWTH OF MICROORGANISMS USING NITROALKYL THIOCYANATES

BACKGROUND OF THE INVENTION

This invention relates to a composition of antimicrobial agents. In a particular aspect this invention relates to an antimicrobial composition useful for controlling the growth of microorganisms.

One of the problems in metal working industries is the susceptibility of metal working fluids (which are emulsions of oil or chemical lubricants in water) to microbial attack. Were it not for this microbial contamination, the oil could be used for many months, but actually the microbial growth shortens the working life of the oil considerably. Microbial action may cause the emulsion to break and become acidic, thus causing corrosion problems. Some of the microbes may be pathogenic which can cause skin infections and other industrial health problems. In addition the microbial mycelia can clog pumps and valves, and often a foul odor develops. In a large installation, frequent replacement of metal working fluids is costly.

SUMMARY OF THE INVENTION

It is an object of this invention to provide an antimicrobial composition.

It is another object of this invention to provide an antimicrobial composition having particular utility in aqueous systems.

Other objects will be apparent to those skilled in the art from the description herein.

It is the discovery of this invention to provide a compound represented by the formula:

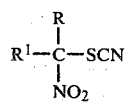

wherein R is hydrogen or methyl, $R^1$ is hydrogen, methyl or ethyl, or R and $R^1$ can collectively be a cyclic alkyl group of 5 carbon atoms; such a compound is useful for controlling the growth of microorganisms by applying the compound to them or to the environment inhabited by them.

DETAILED DESCRIPTION

The compounds of the present invention are effective for controlling the growth of a wide variety of microorganisms. They are generally effective to combat the growth of microorganisms at a concentration of at least about 500 ppm. However, depending on the vigor of the organisms, the length of time during which growth should be suppressed, etc., concentrations of about 1000 ppm or even up to 1500 or 2000 ppm may be preferred.

The compounds of the present invention are prepared by reacting the sodium or potassium salt of the aci-form of a nitroalkane (i.e., the salt of alkylnitronic acid) with thiocyanogen. The reaction proceeds readily in the cold. Preferably the reactants are suspended in an organic liquid such as toluene. The products are oils which can be purified by vacuum distillation.

Thiocyanogen can be supplied by any source thereof, e.g. cupric thiocyanate, which by converting to cuprous thiocyanate, releases thiocyanogen. Cupric thiocyanate is a known compound and can be prepared by the method of J. L. Wood, "Organic Reactions", Volume III, Roger Adams, ed. p. 257 (1946).

Nitroalkanes which can be used to form the salt of alkylnitronic acid include those of from 1 to 3 carbon atoms and nitrocyclohexane. The salts of nitromethane (or, more properly, methylnitronic acid) and nitroethane are unstable and dangerous. The salt of nitromethane is especially so and detonates readily. Consequently, when these salts are being used, care should be taken to maintain them in solution or suspension and not permit them to become dry.

The method of controlling the growth of microorganisms of this invention comprises application of an antimicrobial compound represented by the above formula to a substratum infested with the microorganisms to be controlled or to a substratum to be protected from infestation with the microorganisms. The term substratum as used herein is intended to mean the environment or medium upon which an organism grows and includes both animate and inanimate matter, such as animal and vegetable living or dead, and the soil. The terms microbe and microorganism as used herein are intended to include bacteria and fungi. The term antimicrobial as used herein is intended to include the terms bactericidal, bacteriostatic, fungicidal and fungistatic. No attempt has been made to determine if the products actually cause the death of the organism or merely prevent their growth. The compounds are especially useful in cutting oils for metal working, latex paints, and recirculated cooling water.

The compounds of this invention are soluble in organic solvents such as aliphatic alcohols and ketones and can be employed as a non-aqueous solution if desired. Also, if preferred, the compounds can be used as such without dilution.

In controlling the growth of microorganisms the combination of this invention is supplied to the organisms or to their environment in a lethal or toxic amount. This can be done by dispersing a compound or mixture thereof, or a composition containing it, in, on or over an environment or substratum infested with, or to be protected from, the microorganisms. A compound of this invention or a mixture containing it can be dispersed in any conventional method which permits contact between the organisms and the antimicrobial agents of this invention. The system to be protected may contain a compound of this invention added by the manufacturer at the time of manufacture or preparation. Alternatively, the proper amount of the compound can be added ad libitum.

The invention will be better understood with reference to the following examples. It is understood that the examples are intended to be illustrative only and it is not intended that the invention be limited thereby.

EXAMPLE 1

2-Nitropropane 20 g (0.225 moles) was dissolved in 200 ml of methanol and sodium methoxide 11 g (0.203 moles) was added. The mixture was evaporated at 60 mm and 43° C. Cyclohexane 125 ml was added and the mixture was again evaporated at 25 mm and 43° C., giving sodium 2-propanenitronate. The salt was then dispersed in 150 ml toluene. Cupric thiocyanate 75.4 g was dispersed in 150 ml of toluene and chilled to 5° C. The sodium 2-propanenitronate mixture was added and the resulting mixture was stirred at 5°–10° C. for 10 minutes and at 31°–33° C. for one hour and filtered.

The filter cake was washed with 100 ml of toluene and two additional washes of 60 ml each. The washings were added to the filtrate and the combination was evaporated on a rotary evaporator yielding a residue of 14.3 g. It was dissolved in 100 ml of methanol and heated with 1 g of decolorizing carbon. After filtration and evaporation at 25 mm and 60° C., there was obtained 13.6 g of crude 1-methyl-1-nitroethyl thiocyanate. Distillation gave material of 97–98% purity (by NMR) boiling at 67° at 1.3 mm to 81° C. at 2.8 mm. It was designated P-2216 for convenience.

The analysis was as follows:

|  | C | H | N | S |
|---|---|---|---|---|
| Found: | 33.77 | 4.26 | 19.15 | 21.52 |
| Calc.: | 32.86 | 4.14 | 19.17 | 21.94 |

The infrared absorption spectrum was consistent with the proposed structure.

The antimicrobial properties were determined by the tube dilution method. Media for the bacterial cultures was trypticase soya broth at pH 7.3 prepared as known in the art, and the media for the fungi was Sabouraud broth at pH 5.6, also prepared as known in the art. The inoculum was standardized by the pour plate method for a total viable organism count. The amount of the inoculum per tube was 5 ml at a population of 105 organisms per ml.

The compound was tested for antibacterial and antifungal activity against eight bacteria and four fungi. The results are listed in Table 1. They are reported as minimum inhibitory concentration, which is the range between the highest concentration which permits growth and the lowest concentration which prevents growth. They increase exponentially. Because of uncontrollable variables, such as the vigor of the organism, the data are reproducible to about plus or minus one range.

Table 1
Antimicrobial Activity

|  | Inhibitory Concn, μg/ml | |
|---|---|---|
| Microorganism | P-2216 | P-2217 |
| BACTERIA | | |
| *Staphyloccus aureus* | 1–10 | 1–10 |
| *Streptococcus fecalis* | 50–100 | 50–100 |
| *Streptococcus hemolyticus* | 50–100 | 50–100 |
| *Escherichia coli* | 10–50 | 10–50 |
| *Pasteurella pseudotuberculosis* | 1–10 | 10–50 |
| *Pseudomonas aeruginosa* | 10–50 | 10–50 |
| *Shigella dysenteriae* | 10–50 | 50–100 |
| *Mycobacterium ranae* | 1–10 | 1–10 |
| FUNGI | | |
| *Aspergillus niger* | 10–50 | 10–50 |
| *Candida albicans* | 1–10 | 10–50 |
| *Penicillium sp.* | 10–50 | 10–50 |
| *Aspergillus fumigatus* | 1–10 | 1–10 |

A cutting oil emulsion is prepared according to the following formula:

| Light mineral oil | 20 parts |
|---|---|
| Water | 76.9 |
| P-2216 | 0.1 |
| Emulsifying agent | 3 |
|  | 100 |

The emulsion remains free from microbial contamination for a long period of time when used as a cutting oil.

The LD50 in mice by oral administration was determined to be 500 mg/kg.

EXAMPLE 2

The experiment of Example 1 is repeated in all essential details except that 1-nitropropane is substituted for 2-nitropropane and sodium 1-propanenitronate is obtained. There is obtained 1-nitropropyl thiocyanate, designated P-2216. It is tested for antimicrobial activity and is found to be effective against a wide spectrum of bacteria and fungi. When incorporated in metal working fluids at 500-1000 ppm or more, it controls the growth of microorganisms for a prolonged period.

EXAMPLE 3

The experiment of Example 1 is repeated in all essential details except that nitroethane is substituted for 2-nitropropane and sodium ethanenitronate is obtained. The latter compound is considered to be unstable and hazardous so is not evaporated to dryness as was the propane-nitronate. When reacted with cupric thiocyanate, there is obtained 1-nitroethyl thiocyanate. It is tested for antimicrobial activity and is found to be effective against a wide spectrum of bacteria and fungi. When incorporated in metal working fluids at 500-1000 ppm or more, it controls the growth of microorganisms for a prolonged period.

EXAMPLE 4

The experiment of Example 1 is repeated in all essential details except that nitromethane is substituted for 2-nitropropane and sodium methanenitronate is obtained. The latter compound is known to be very unstable and highly explosive. Care is taken not to allow it to evaporate to dryness. When reacted with cupric thiocyanate, there is obtained nitromethyl thiocyanate. It is tested for antimicrobial activity and is found to be effective against a wide spectrum of bacteria and fungi. When incorporated in metal working fluids at 500-1000 ppm or more, it controls the growth of microorganisms for a prolonged period.

EXAMPLE 5

The experiment of Example 1 was repeated in all essential details except that nitrocyclohexane was substituted for 2-nitropropane on an equimolar basis. The product was not distilled but was purified by multiple chromatography on silica gel plates using hexane and carbon tetrachloride as developing solvents. There was obtained 1-nitrocyclohexyl thiocyanate, designated P-2217. It analyzed

|  | C | H | N | S |
|---|---|---|---|---|
| Calc.: | 45.14 | 5.41 | 15.05 | 17.22 |
| Found: | 45.74 | 5.59 | 14.71 | 16.96 |

The infrared absorption spectrum was consistent with the proposed structure. It was tested for antimicrobial activity and found to be effective against both bacteria and fungi as shown by the data in the table. The oral LD50 was 150 mg/kg. It is tested for antimicrobial activity and is found to be effective against a wide spectrum of bacteria and fungi. When incorporated in metal working fluids at 500–1000 ppm or more, it controls the growth of microorganisms for a prolonged period.

I claim:

1. A nitroalkyl thiocyanate represented by the formula

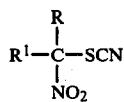

wherein R is hydrogen or methyl, $R^1$ is hydrogen, methyl or ethyl, or R and $R^1$ can collectively be a cyclic alkyl group of 5 carbon atoms.

2. A method of controlling the growth of bacteria and fungi by applying to them or to the environment inhabited by them a compound represented by the formula

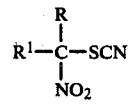

wherein R is hydrogen or methyl, $R^1$ is hydrogen, methyl or ethyl, or R and $R^1$ can collectively be a cyclic alkyl group of 5 carbon atoms.

3. A compound of claim 1 wherein R and $R^1$ are methyl.

4. A compound of claim 1 wherein R and $R^1$ are hydrogen.

5. A compound of claim 1 wherein R is hydrogen and $R^1$ is ethyl.

6. A compound of claim 1 wherein R is hydrogen and $R^1$ is methyl.

7. A compound of claim 1 wherein R and $R^1$ collectively form a cyclic alkyl group of 5 carbon atoms.

* * * * *

UNITED STATES PATENT AND TRADEMARK OFFICE
CERTIFICATE OF CORRECTION

PATENT NO. : 4,200,646
DATED : April 29, 1980
INVENTOR(S) : Herbert L. Wehrmeister It is certified that error appears in the above-identified patent and that said Letters Patent are hereby corrected as shown below:

Column 3, line 29, "105" should read -- $10^5$ --

Signed and Sealed this

Twenty-fifth Day of November 1980

[SEAL]

Attest:

SIDNEY A. DIAMOND

Attesting Officer

Commissioner of Patents and Trademarks